(12) United States Patent
Swisher et al.

(10) Patent No.: US 11,918,412 B2
(45) Date of Patent: Mar. 5, 2024

(54) GENERATING A SIMULATED IMAGE OF A BABY

(71) Applicant: KONINKLIJKE PHILIPS N.V., Eindhoven (NL)

(72) Inventors: Christine Menking Swisher, San Diego, CA (US); Claudia Errico, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 687 days.

(21) Appl. No.: 17/052,262

(22) PCT Filed: Apr. 26, 2019

(86) PCT No.: PCT/EP2019/060735
§ 371 (c)(1),
(2) Date: Nov. 2, 2020

(87) PCT Pub. No.: WO2019/211186
PCT Pub. Date: Nov. 7, 2019

(65) Prior Publication Data
US 2021/0077063 A1 Mar. 18, 2021

Related U.S. Application Data

(60) Provisional application No. 62/665,612, filed on May 2, 2018.

(51) Int. Cl.
*A61B 8/08* (2006.01)
*G06N 20/00* (2019.01)

(52) U.S. Cl.
CPC .......... *A61B 8/0866* (2013.01); *A61B 8/5207* (2013.01); *G06N 20/00* (2019.01)

(58) Field of Classification Search
CPC .... A61B 8/0866; A61B 8/5207; G06N 20/00; G06T 11/00; G06T 11/006
See application file for complete search history.

(56) References Cited

U.S. PATENT DOCUMENTS 8,012,091 B2  9/2011  Petraglia
9,820,717 B2  11/2017 Smillie
(Continued)

FOREIGN PATENT DOCUMENTS

JP  2007325786 A  12/2007
JP  2017221269 A  12/2017
(Continued)

OTHER PUBLICATIONS

International Search Report and Written Opinion for International Application No. PCT/EP2019/060735, filed Apr. 26, 2019, 15 pages.
(Continued)

*Primary Examiner* — Boniface N Nganga

(57) ABSTRACT

Systems and computer implemented method of generating a simulated image of a baby based on an ultrasound image of a fetus. A method comprises acquiring an ultrasound image of the fetus, and using a machine learning model to generate the simulated image of the baby, based on the ultrasound image of the fetus, wherein the simulated image of the baby comprises a prediction of how the fetus will look as a baby.

14 Claims, 7 Drawing Sheets

(56) References Cited

U.S. PATENT DOCUMENTS

| | | | |
|---|---|---|---|
| 10,424,087 B2 | 9/2019 | Risser | |
| 2013/0004036 A1 | 1/2013 | Apelbaum et al. | |
| 2017/0230675 A1 | 8/2017 | Wierstra | |
| 2019/0114462 A1* | 4/2019 | Jang | G06N 3/084 |

FOREIGN PATENT DOCUMENTS

| | | |
|---|---|---|
| WO | 2008114937 A1 | 9/2008 |
| WO | 2018075927 A1 | 4/2018 |

OTHER PUBLICATIONS

Anonymous: "Alethio is a specialist in image analysis systems", Economy Current, Dec. 3, 2018, Retrieved from the Internet: URL:http://world.kbs.CO,kr/service/contents_view.htm?1ang=g&menu_cate=business&i d=&bpard_seq=352887#none, pp. 1-6. (Abstract).

Goodfellow et al. Generative Adversarial Nets. (2014), Advances in Neural Information Processing Systems 27 (NIPS 2014), pp. 1-9.

Radford et al. "Unsupervised Representation Learning with Deep Convolutional Generative Adversarial Networks", ICLR (2016), pp. 1-16.

Dumoulin et al. "A learned Representation for Artistic Style", Computer Vision and Pattern Recognition, Feb. 9, 2017, . ICLR (2017), pp. 1-26.

Zhang, Z. et al., "Age Progression/Regression by Conditional Adversarial Autoencoder," 2017 IEEE Conference on Computer Vision and Pattern Recognition (CVPR), 2017, pp. 4352-4360.

\* cited by examiner

GENERATING A SIMULATED IMAGE OF A BABY

RELATED APPLICATIONS

This application is the U.S. National Phase application under 35 U.S.C. § 371 of International Application No. PCT/EP2019/060735, filed on Apr. 26, 2019, which claims the benefit and priority to Provisional Application No. 62/665,612, filed May 2, 2018. These applications are hereby incorporated by reference herein, for all purposes.

TECHNICAL FIELD

Embodiments herein relate to generating a simulated image of a baby, based on an ultrasound image of a fetus.

BACKGROUND

The general background of the disclosure herein is in prenatal imaging of fetuses. Prospective parents are often interested in the appearance of their growing baby. One way of imaging a fetus in utero is through the use of ultrasound imaging in 2D, 3D or 4D. 3D and 4D ultrasound allows parents to see unborn babies in more depth than standard 2D fetal sonography examinations. In brief, a 3D fetal scan can be thought of as multiple two-dimensional images that are taken at various angles to form a three-dimensional rendering. A 4D ultrasound scan shows movement and gives a real time video of the baby.

3D and 4D pre-natal ultrasound provides an exciting experience for parents and family members, however, the images may not look realistic, despite the latest ultrasound technology.

SUMMARY

As described above, despite advances in ultrasound technology, the images produced by ultrasound may not be very representative of how a fetus looks in real life, nor how a fetus may look when born. Parents are naturally interested in the appearance of their fetuses and therefore there is a desire to produce more life-like images.

Therefore, according to a first aspect there is a computer implemented method of generating a simulated image of a baby based on an ultrasound image of a fetus. The method comprises acquiring an ultrasound image of the fetus, and using a machine learning model to generate the simulated image of the baby, based on the ultrasound image of the fetus, wherein the simulated image of the baby comprises a prediction of how the fetus will look as a baby.

According to a second aspect there is a computer implemented method of training a machine learning model to produce a simulated image of a baby based on an ultrasound image of a fetus. The method comprises providing example ultrasound images of fetuses and corresponding example images of the same fetuses as babies, and training the machine learning model, using the example images, to produce a simulated image of a baby for an ultrasound image of a fetus, wherein the simulated image of the baby comprises a prediction of how the fetus will look as a baby.

According to a third aspect there is a computer program product comprising a non-transitory computer readable medium, the computer readable medium having computer readable code embodied therein, the computer readable code being configured such that, on execution by a suitable computer or processor, the computer or processor is caused to perform the method of the first aspect or the second aspect.

According to a fourth aspect there is a system for generating a simulated image of a baby based on an ultrasound image of a fetus. The system comprises a memory comprising instruction data representing a set of instructions and a processor configured to communicate with the memory and to execute the set of instructions. The set of instructions, when executed by the processor, cause the processor to acquire an ultrasound image of the fetus, and use a machine learning model to generate the simulated image of the baby, based on the ultrasound image of the fetus, wherein the simulated image of the baby comprises a prediction of how the fetus will look as a baby.

In this way, a machine learning model may be trained and used to take an ultrasound image of a fetus and provide a simulated image that predicts how the fetus may look when born. As such, the systems and methods herein may provide an improved way for parents of the fetus to view and envisage the appearance of their baby after birth. This may help with parent-child bonding.

These and other aspects will be apparent from and elucidated with reference to the embodiments described hereinafter.

BRIEF DESCRIPTION OF THE DRAWINGS

For a better understanding of the embodiments herein, and to show more clearly how they may be carried into effect, reference will now be made, by way of example only, to the accompanying drawings, in which.

DETAILED DESCRIPTION OF EMBODIMENTS

As described above, parents are naturally interested in the appearance of an unborn fetus. Ultrasound images may provide some clues as to the appearance of the fetus, however these may be grainy and generally of poor quality. It is an object of embodiments herein to provide a simulated image of a baby that predicts or provides an example illustration of how a fetus imaged in ultrasound may look when born.

Figure 1:
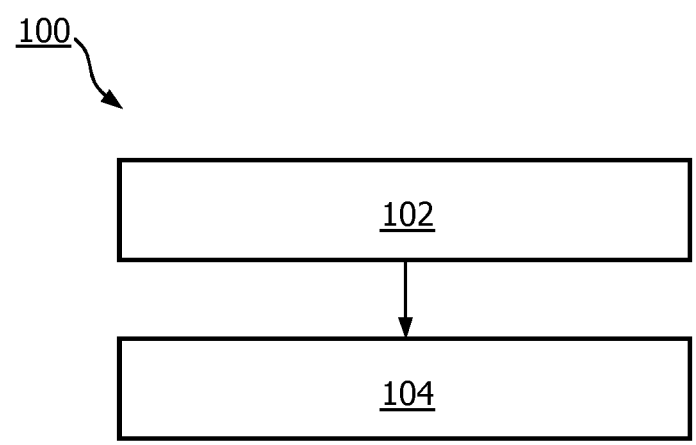
FIG. 1 shows a flowchart of an example computer implemented method of generating a simulated image of a baby based on an ultrasound image of a fetus according to some embodiments.

FIG. 1 illustrates a computer implemented method of generating a simulated image of a baby based on an ultrasound image of a fetus according to some example embodiments herein. The method comprises in a first block 102, acquiring an ultrasound image of the fetus and in a second block 104, using a machine learning model to generate the simulated image of the baby, based on the ultrasound image of the fetus, wherein the simulated image of the baby comprises a prediction of how the fetus will look as a baby.

As will be described in more detail below, the method 100 may be performed, for example, by a computing device such as computer, tablet computer or mobile phone. The method 100 may be performed, for example, by an application (or "app") installed on such a computing device.

In some embodiments, the block 102 of acquiring an ultrasound image may comprise acquiring an ultrasound image from a database of ultrasound images. In other embodiments, the block 102 of acquiring an ultrasound image may comprise taking ultrasound data (e.g. making ultrasound measurements), for example, using an ultrasound scanner.

The ultrasound image may be of any dimensionality. For example, the ultrasound image may comprise a 2D, 3D or 4D (e.g. 3 spatial dimensions and a time dimension) image. In some embodiments, the ultrasound image may be generated from three-dimensional or four-dimensional data. In some embodiments the method 100 may further comprise processing such three-dimensional or four-dimensional data to produce the ultrasound image.

Figure 2:
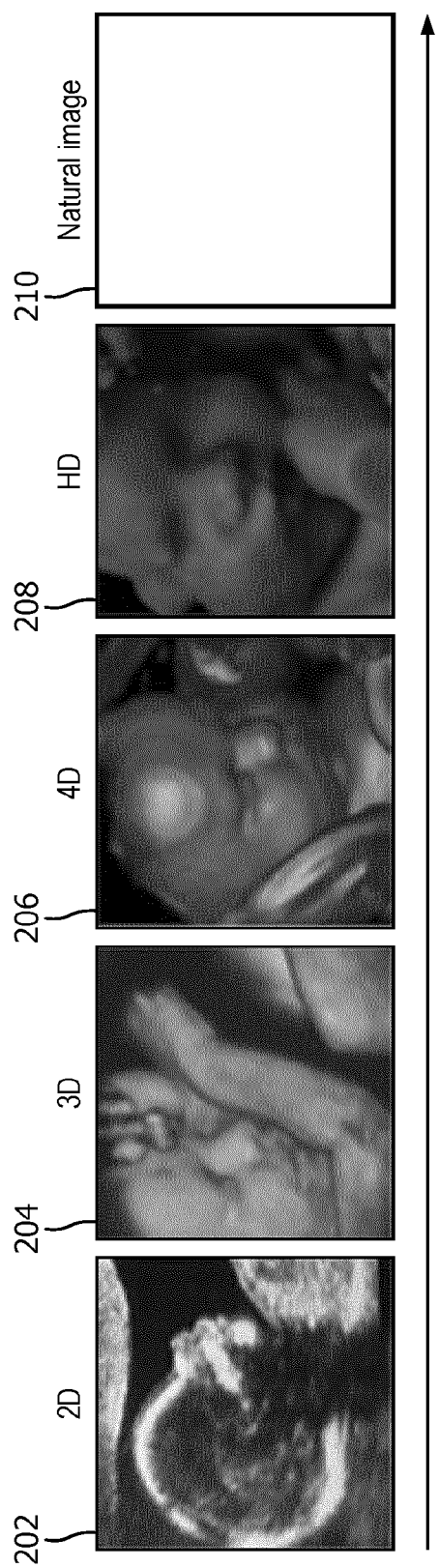
FIG. 2 shows examples of different types of ultrasound images of fetuses.

Examples of some of the types of ultrasound images that may be provided as input to the machine learning model are provided in FIG. 2 which shows example 2D, 3D, 4D and HD (high definition) images of a fetus, as denoted by numerals 202, 204, 206 and 208 respectively. It is an object of the embodiments herein to improve on these types of images. It is an object of some embodiments herein to provide a life-like or natural image of a baby 210.

In block 104, as noted above, the method comprises using a machine learning model to generate the simulated image of the baby, based on the ultrasound image of the fetus, wherein the simulated image of the baby comprises a prediction of how the fetus will look as a baby.

In other words, in block 104, a machine learning model (e.g. a trained machine learning model) takes the ultrasound image of the fetus as input and produces a simulated image of a baby, based on the ultrasound image of the fetus.

The machine learning model may comprise any type of machine learning model that may take image data (e.g. an ultrasound image) as input and produce a simulated image as output. The skilled person will generally be familiar with machine learning models suitable for image manipulation. Examples of some types of machine learning model that may be deployed in embodiments herein are described in detail below, but in brief, in some embodiments, the machine learning model may comprise a neural network such as a convolutional neural network, a variational Autoencoder (VAE) or a Neural Artistic Style transfer network. The skilled person will appreciate that these are merely examples however and that other machine learning models may also be used.

The machine learning model has been trained to take an ultrasound image of a fetus as input and output a simulated image of a baby. In some embodiments (and as will be described in more detail below), the machine learning model has been trained using example ultrasound images of fetuses and corresponding example (photographic) images of the same fetuses as babies. The machine learning model may have been trained, using such pairs of example images to predict the simulated image of a baby from the ultrasound image of a fetus.

The simulated image of the baby comprises a prediction of how the fetus will (or may) look as a baby. For example, the simulated image may comprise an image that provides an example, or example illustration, of how the fetus could look when born. The skilled person will appreciate that the simulated image may not necessarily comprise an accurate prediction, rather, in some examples, the simulated image may be provided for illustrative or entertainment purposes.

The simulated image may comprise any image that provides a prediction of how the fetus will look after birth. For example, the simulated image may comprise an image that provides a prediction of how the fetus will look immediately after birth, in the age range 0-3 months, in the age range 3-12 months, or in any other age range after birth. In this sense, "simulated" may mean, for example, that the image is enhanced, improved, altered or combined with other data or other images in order to provide a prediction of how the fetus will look as a baby.

The simulated image may comprise an image of photographic quality. For example, in some embodiments, the simulated image may comprise a simulated photographic image. Such a simulated photographic image may have the appearance of being captured by a digital camera, film camera (e.g. using photographic film), or similar medium or device. As such, in some embodiments, the simulated image may comprise a life-like photographic-style image of a baby. As such, some embodiments herein may be used to generate a photograph from an ultrasound image.

The simulated image may be a black and white image (e.g. a black and white photographic image) or a color image (e.g. a color photographic image).

In some embodiments, other information (e.g. in addition to the ultrasound image of the fetus) may be used or provided as inputs to the machine learning model for use by the machine learning model in producing the simulated image of the baby. For example, the method 100 may further comprise acquiring supplementary data relating to a parent of the fetus. The block 104 of using a machine learning model to generate the simulated image of the baby may further be based on the supplementary data (e.g. the supplementary data may be an additional input to the machine learning model).

The supplementary data relating to a parent of the fetus may comprise, for example, a characteristic of the parent. Examples of characteristics of the parent may comprise, for example, physical characteristics such as eye color, hair color or skin tone. Other examples include demographic data, for example, the ethnicity of a parent. In this way, characteristics or characteristic features associated with a parent of the fetus may be used by the machine learning model to predict the appearance of the fetus as a baby.

In some embodiments, the supplementary data relating to a parent of the fetus may comprise a photographic image of a parent as a baby. Such a photographic image may comprise a black and white photographic image or a color photographic image. As such, photographs of a parent may be input into the machine learning model, so that the machine learning model may incorporate photographic features of a parent of the fetus into the simulated image of the baby.

In some embodiments, the machine learning model may generate the simulated image of the baby by combining one or more features of the ultrasound image of the fetus with one or more features derived from the supplementary data.

In this way, parental data or images of the parent as a baby may be combined with an ultrasound image of the fetus to provide a prediction of how the fetus may look as a baby. It will be appreciated that in practice, any characteristics or images of babies (e.g. characteristics or images of siblings, other relatives or even unrelated babies) may be used as supplementary data. However, it may be desirable, in order to provide a more accurate prediction of the appearance of the fetus as a baby, for the supplementary data to be representative of a close genetic match to the fetus e.g. such as a parent.

In some embodiments, the machine learning model may comprise a variational autoencoder. The skilled person will be familiar with variational autoencoders, but in brief, a variational autoencoder consists of two neural networks. The first neural network acts as an encoder, and the second neural network acts as a decoder. The variational autoencoder also comprises a loss function. The encoder compresses the data (e.g. 28×28 image; 784-dimension) into a "Latent Space", Z, with a much lower dimensionality. The decoder reconstructs the data given the hidden representation. Typically, encoders are trained to learn an efficient compression of the data in order for the decoder to accurately re-create the original image. Decoders may also be trained to apply features (e.g. objects or styles) that aren't present in the original image. As such, variational autoencoders may generally be applied where there is paired information such as before and after photographs.

In embodiments herein, it has been appreciated that a compressed version of an ultrasound image of a fetus, as produced by such an encoder, may be used as a representation of the most meaningful features. These meaningful features may then be enhanced (e.g. using features from the parent) to create the simulated photographic image of the parent.

Thus, in embodiments herein, the ultrasound image of the fetus may be provided to the encoder which compresses the ultrasound image into a lower dimensionality representation. The lower dimensionality representation comprises less data than the ultrasound image. This may be thought of as extracting features (e.g. the most important or most salient features) of the ultrasound image. The decoder may then reconstruct a new image from the lower dimensionality representation (e.g. the features) and any supplementary data relating to a parent of the fetus.

Put another way, the block 104 of using a machine learning model to generate the simulated image of the baby may comprise the machine learning model compressing the ultrasound image to determine the one or more features of the ultrasound image, and generating the simulated image of the baby by reconstructing the one or more features of the ultrasound image, using (e.g. incorporating) the supplementary data.

Compressing the ultrasound image may comprise encoding the ultrasound image into a lower dimensionality space in one or more lower layers of a variational autoencoder. Generating the augmented image of the fetus may comprise inserting the supplementary data into a hidden layer of the variational autoencoder and decoding the compressed ultrasound image.

In this way, the supplementary data of the parent may be inserted into a variational autoencoder to enable the supplementary data to be combined with features derived from a compression of an ultrasound image of a fetus in order to produce a simulated image of a baby. In this way, the simulated image of the baby comprises a prediction of how the fetus will (or may) look as a baby, based on the ultrasound image and parental information.

Figure 3:
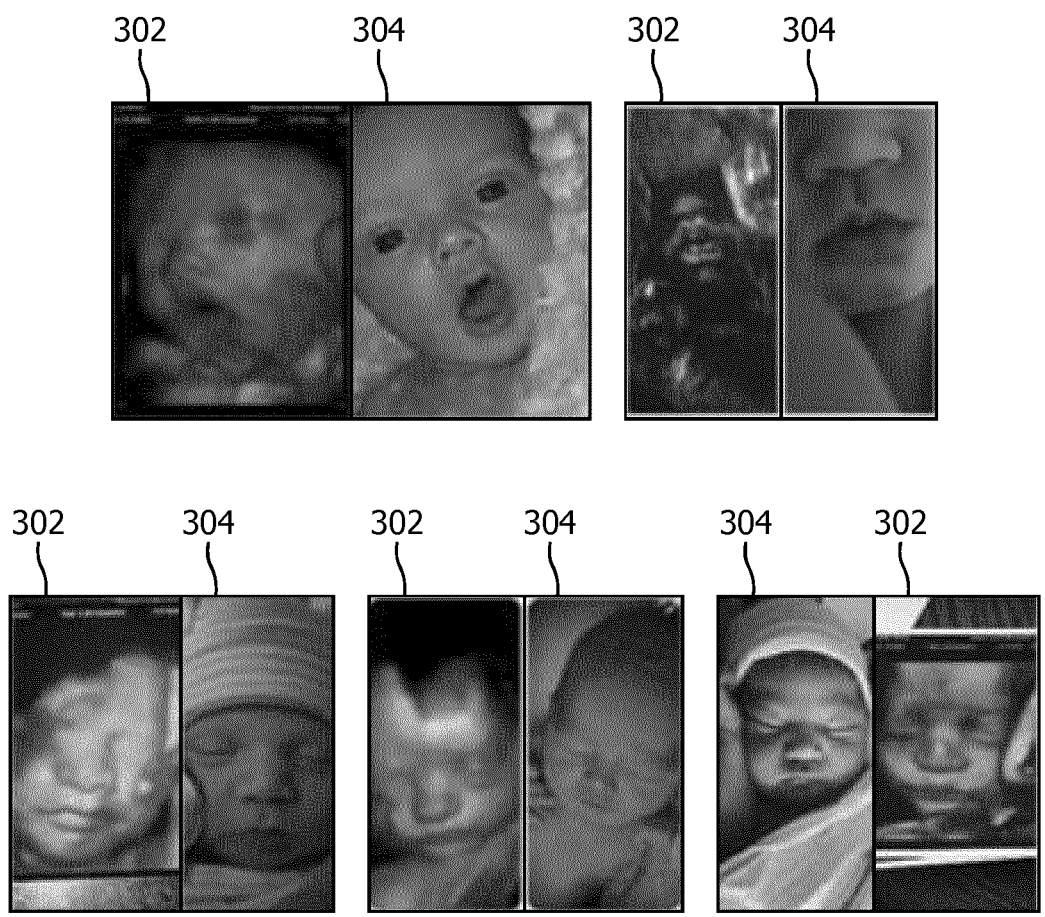
FIG. 3 shows example image pairs that may be used to train a machine learning model to produce a simulated image that is predictive of how a fetus may look as a baby.

Turning now to FIG. 3, in one example embodiment, a variational autoencoder may be trained using training data comprising image pairs such as those shown in FIG. 3. Each image pair comprises an ultrasound image 302 of a fetus and a corresponding example photographic image of the same fetus as a baby (e.g. after birth) 304. The variational autoencoder is trained, using the example image pairs as training data. The example ultrasound images of fetuses are thus examples of input data and the example photographic images are examples of corresponding outputs, e.g. ground truth.

In some embodiments, the machine learning model may be trained using training data comprising example images that cover many different populations of babies (e.g. babies having parents with different combinations of ethnicities, eye colors, hair colors etc.).

In some embodiments, the training data may be annotated with the characteristics of the parent which can then be used as input parameters to the machine learning model. As such, during training, once the characteristics of the parent(s) are determined (e.g. white, Japanese, etc.), the machine learning model may distribute (e.g. set the values of) the weights to make this information more relevant to the output.

In one example, the machine learning model design comprises a variational autoencoder in the form of an encoder-decoder network. The inputs comprise a gray scale image and supplementary data comprising a parent demographic. The model is trained to predict (produce or generate) the image of the baby from the ultrasound images 302 and the supplementary data. In this embodiment, the training is performed using training data e.g. such as the example image pairs 302, 304. The mean and variance may be output from the variational autoencoder and optimized.

Figure 4:
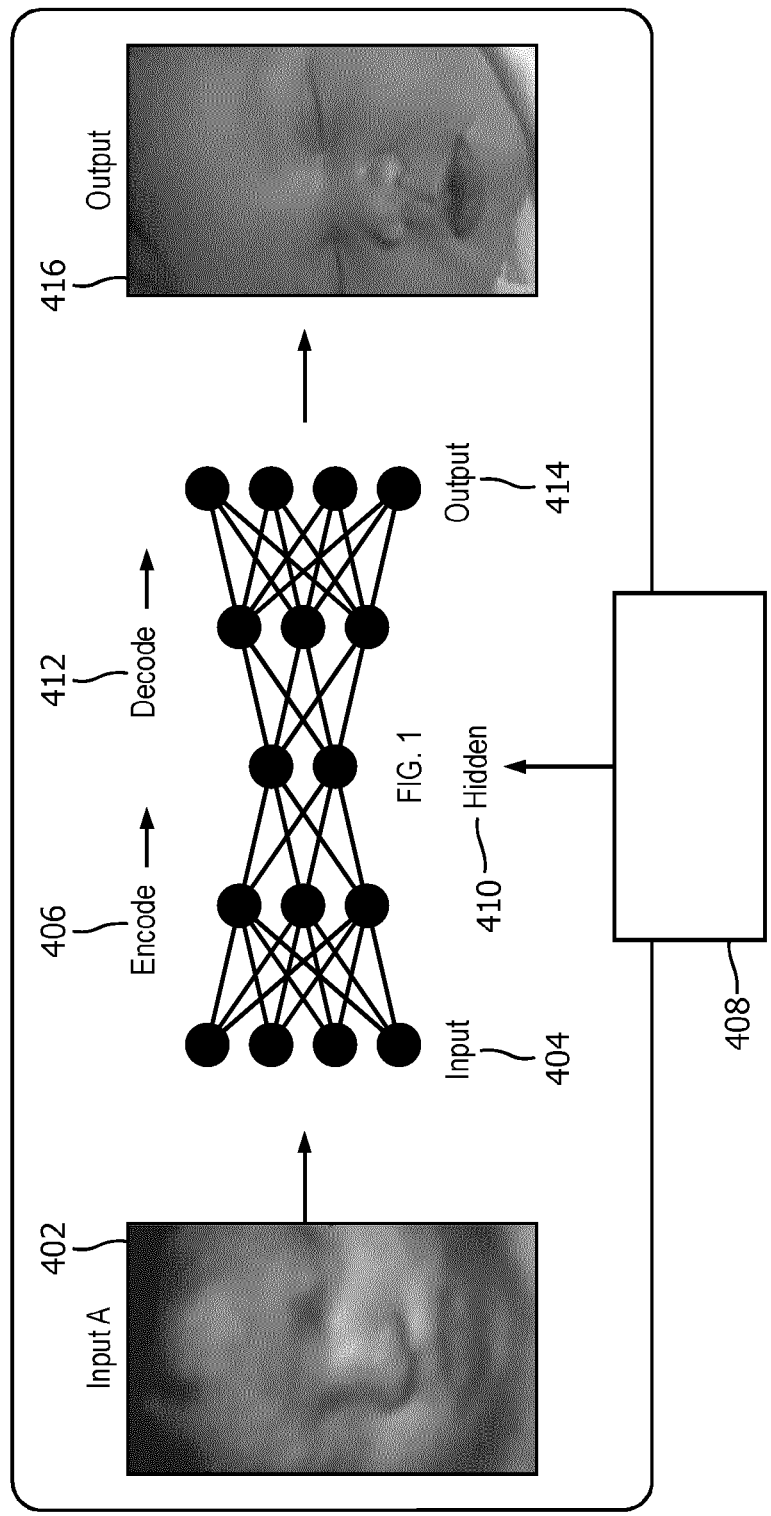
FIG. 4 illustrates an example machine learning model for use in generating a simulated image of a baby based on an ultrasound image of a fetus.

FIG. 4 provides a summary of an example embodiment wherein the machine learning model comprises a deep neural network generative encoder-decoder model. In this embodiment, an ultrasound image 402 is provided as input 404 to the encoder 406 which compresses the ultrasound image. One or more characteristics of the parent 408 may be inserted into a hidden layer 410 of the model. A decoder 412 decodes the compressed ultrasound image to produce an output 414 comprising a simulated image 416 of the baby (e.g. a simulated image representing a prediction of how the fetus in the ultrasound image may look as a baby).

Other types of machine learning model may also be used herein. For example, in some embodiments, the machine learning model may use neural artistic style transfer to generate the simulated image of the baby. Neural artistic style transfer will be familiar to the skilled person and is described in detail in the paper entitled "Image Style Transfer Using Convolution Neural Networks" by Gatys et al. In brief, neural artistic style transfer comprises taking the style (e.g. texture) of one image and applying it to the content (e.g. shapes and structural features) of a second image. In this way, for example, as shown in the Gatys et al. paper, the artistic style of a fine art painter such as Turner may be applied to ordinary photographs to create a representative image describing how Turner may have painted the same scene.

Generally, when neural networks are trained in object recognition for images, each layer in the neural network produces a representation of the image at a different scale. For example, lower layers of neural network produce a representation of the background textures or features, whilst higher levels produce representations that reflect larger scale features (such as object outlines in the image). As such, the style of an image may be determined using the representation of the image from one or more lower layers of a neural network whilst the content may be determined using the representation of the image from one or more higher layers of a neural network.

Herein therefore, in some embodiments, the supplementary data may comprise a photographic image of the parent as a baby and using 104 a machine learning model to generate the simulated image of the baby may comprise the machine learning model determining a style related to the photographic image of the parent as a baby, determining a content of the ultrasound image, and generating the simulated image of the baby by combining the style related to the image of the parent as a baby with the content of the ultrasound image. The skilled person will appreciate that although generally the supplementary data will relate to a parent or other relative of a fetus (e.g. in order to produce a more accurate representation of how the fetus will look when born), in principle, any image of a baby may be used e.g. for entertainment or other purposes. It will be appreciated that the use of other images in this way may produce a less accurate image of how the fetus will look as a baby.

In some embodiments, the machine learning model comprises a neural network model and determining a style related to the image of the parent as a baby may comprise determining a style from one or more representations of the image of the parent as a baby in one or more lower layers of the neural network model.

Determining the content of the ultrasound image may comprise determining the content from one or more representations of the ultrasound image in one or more higher layers of the neural network model.

In this way, style features of the image of the parent, such as skin tone, quality and crispness of the image (e.g. photographic qualities) may be applied to the ultrasound image of the fetus to produce the simulated image of the fetus as a baby.

In embodiments where the machine learning model uses neural artistic style transfer, the machine learning model may comprise two trained convolutional neural networks. One trained on ultrasound images and one trained on the style images. They may be trained using a Loss function of the form:

$$\mathcal{L}_{total}(\vec{p}, \vec{a}, \vec{x}) = \alpha \mathcal{L}_{content}(\vec{p}, \vec{x}) + \beta \mathcal{L}_{style}(\vec{a}, \vec{x})$$

where $\vec{p}$ represents the ultrasound image of the baby, $\vec{a}$ represents the image of the parent of the baby and $\vec{x}$ represents the output simulated image representing the prediction of how the fetus may look as a baby. $\alpha$ and $\beta$ represent weighting factors for the content (from the ultrasound image) and the style (from the image of the parent as a baby) respectively.

There may be no ground truth in the training processes. For example the gradient may be used to iteratively update the image until it simultaneously (e.g. equally) matches the style features of the style image and the content features of the content ultrasound image. The relative proportions in which the content and style contribute to the output simulated image may be changed by altering $\alpha$ and $\beta$.

In some embodiments, a characteristic of the parent, such as any of the characteristics described above may additionally be provided as input.

Figure 5:
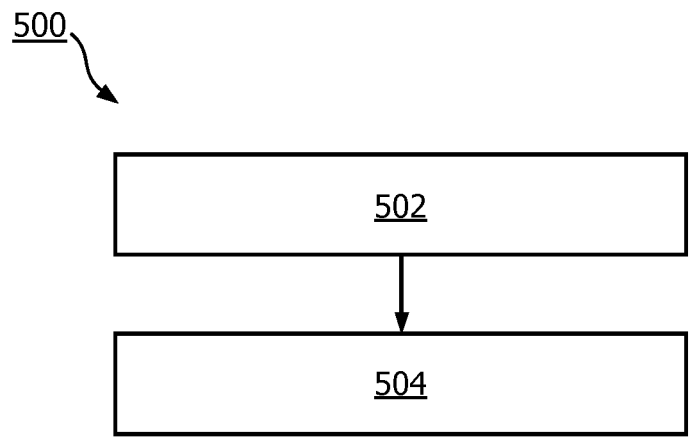
FIG. 5 illustrates a method of training a machine learning model to produce a simulated image of a baby based on an ultrasound image of a fetus according to an example embodiment.

Turning now to FIG. 5, according to some embodiments, there is a computer implemented method 500 of training a machine learning model to produce (e.g. to be able to produce) a simulated image of a baby based on an ultrasound image of a fetus. The method comprises in a block 502 providing example ultrasound images of fetuses and corresponding example images of the same fetuses as babies. In a block 504 the method comprises training the machine learning model, using the example images, to produce a simulated image of a baby for an ultrasound image of a fetus, wherein the simulated image of the baby comprises a prediction of how the fetus will look as a baby.

The method 500 may be used to train the machine learning model to be able to perform the method 100 described above. E.g. the method 500 may be used to enable the machine learning model to produce a simulated image of a baby from a new (e.g. previously unseen) ultrasound image of a fetus. This may be done, as described above, using example image pairs of ultrasound images and corresponding real (e.g. photographic) images of the same fetuses after birth (e.g. as babies). In such embodiments, the example images are training data for the machine learning model.

It will be appreciated by the skilled person that the training generally occurs before the machine learning model is deployed onsite (e.g. that the machine learning model is trained before it is used by a user such as a clinician or parent). For example, in some embodiments, once deployed, it may generally not be necessary to train the model further.

Different examples of machine learning models were provided above with respect to the method 100 and the examples therein apply equally to the method 500.

The example ultrasound images of fetuses may comprise any of the same type of ultrasound images as were described above with respect to the ultrasound image of a fetus in method 100. In some embodiments, the corresponding example images of the same fetuses as babies may comprise real images, e.g. real photographs of the same fetuses after birth. The corresponding example images of the same fetuses as babies may have be taken at any age. For example, straight after birth, at 0-3 months, 3-12 months or during any other age range.

As noted above, the example ultrasound images of fetuses and corresponding example (real) images of the same fetuses as babies represent training data and as such the example images of the same fetuses as babies represent ground truth for the machine learning model.

The simulated image of a baby was described above with respect to method 100 and the details therein will be understood to apply to the method 500. For example, the simulated image may comprise a simulated photographic image that comprises (or represents) a prediction of how the fetus will look as a baby. In this way, a machine learning model may be trained to provide a predicted image of a baby from an ultrasound image of a fetus.

According to some embodiments, block 502 may further comprise providing supplementary data relating to a parent of the fetus. Block 504 may then comprise training the machine learning model, using the example images and the supplementary data, to produce a simulated image of a baby for an ultrasound image of a fetus. Different types of supplementary data and the manner in which supplementary data may be used by a machine learning model were described above with respect to the method 100 and the details therein will be understood to apply equally to the method 500.

Figure 6:
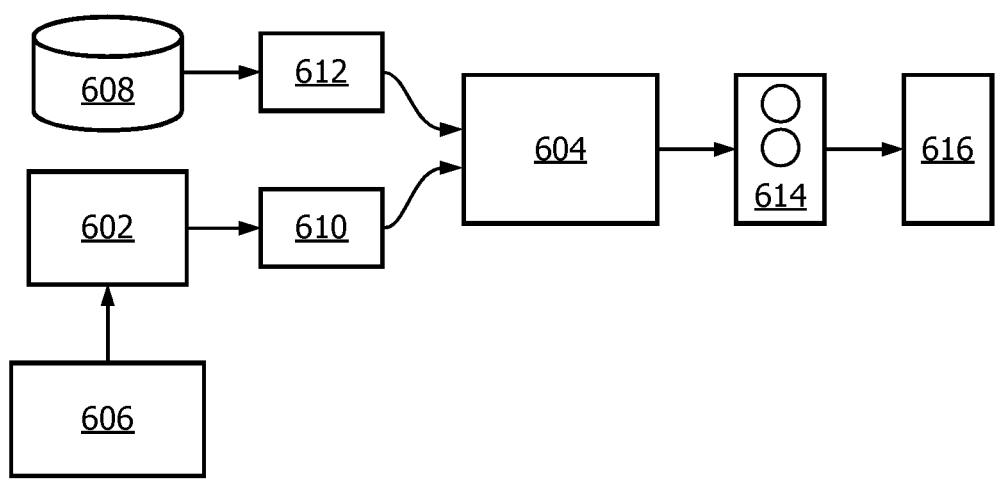
FIG. 6 illustrates an example method of training a machine learning model to produce a simulated image of a baby based on an ultrasound image of a fetus according to an example embodiment.

FIG. 6 illustrates a method according to some embodiments of training a machine learning model to produce a simulated image of a baby based on an ultrasound image of a fetus. This embodiment comprises a generative adversarial network (GAN) comprising a generative model 602 and a discriminator model 604.

The generative model 602 may comprise any type of machine learning model, such as any of the types described above with respect to method 100. For example, the generator may comprise a variational autoencoder, as described above, comprising compression and encoder-decoder networks.

The discriminator model 604 may comprise any type of machine learning model, such as any of the types described above with respect to method 100. For example, the generator may comprise a neural network such as a convolutional neural network based classifier.

An ultrasound image of a fetus 606 is provided to the generator model 602 which outputs a simulated image of a baby 610, based on the input ultrasound image, as was described above with respect to the method 100.

There is further a database 608 comprising real images 612 (e.g. photographic images) of real babies. The discriminator 604 is fed either a real image 612 of a real baby or a simulated image 610 output from the generator. The discriminator estimates the probability that the input image came from the generator as opposed to the database of real images (e.g. the discriminator estimates the probability that a received image comprises a simulated image). The goal of the generator is to produce simulated images of babies 610 of such quality that they are undistinguishable from the real images of babies 612. The discriminator outputs 614 whether the input is real or fake and this updates a loss function 616.

Put another way, the training procedure for the generative model is to maximize the probability of the discriminator making a mistake. This framework corresponds to a minimax two-player game. Training is successful once the generator is able to trick the discriminator.

In more detail, according to one embodiment, the machine learning model may comprise a generator and discriminator pair. The generator may comprise a model similar to a variational autoencoder (as described above) and the discriminator may comprise a convolutional neural network based classifier. The input to the generator may comprise a gray scale ultrasound image and one or more characteristics of a parent, such as demographic information relating to the parent. The output of the generator may comprise a simulated photographic image, e.g. a three channel color image. The machine learning model may be trained using a loss function such as a binary cross-entropy loss function.

More generally, in embodiments where the generator and the discriminator are defined by multilayer perceptrons, the entire system may be trained with backpropagation. As such, in some embodiments there may be no need for Markov chains or unrolled approximate inference networks during either training or generation of samples. Therefore, generative adversarial networks may provide an attractive alternative to maximum likelihood techniques. In addition, their learning process and the lack of a heuristic cost function (such as pixel-wise independent mean-square error) are attractive to representation learning. In healthcare applications such as those described herein, ground truth paired images (e.g. such as ultrasound images of fetuses and corresponding images of the same fetus after birth) may be difficult to acquire. Generative adversarial networks may overcome such issues since they only require good example images in order to improve, without the need for the example images to be paired with corresponding pre-natal ultrasound images.

Figure 7:
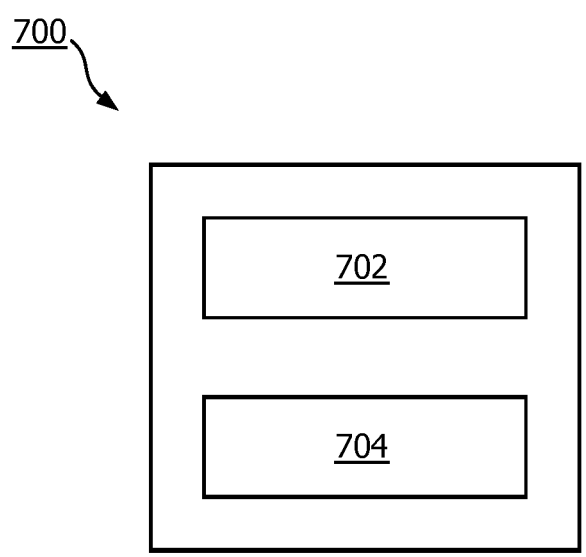
FIG. 7 illustrates an example system for generating a simulated image of a baby based on an ultrasound image of a fetus according to some embodiments.

Turning now to FIG. 7, according to some embodiments, there is a system 700 for generating a simulated image of a baby based on an ultrasound image of a fetus. The system 700 comprises a memory 704 comprising instruction data representing a set of instructions. The system 700 further comprises a processor 702 configured to communicate with the memory 704 and to execute the set of instructions. The set of instructions when executed by the processor may cause the processor to perform any of the embodiments of the methods 100 or 500, as described above.

In some implementations, the instruction data can comprise a plurality of software and/or hardware modules that are each configured to perform, or are for performing, individual or multiple steps of the method described herein. In some embodiments, the memory 704 may be part of a device that also comprises one or more other components of the system 700 (for example, the processor 702 and/or one or more other components of the system 700). In alternative embodiments, the memory 704 may be part of a separate device to the other components of the system 700.

In some embodiments, the memory 704 may comprise a plurality of sub-memories, each sub-memory being capable of storing a piece of instruction data. In some embodiments where the memory 704 comprises a plurality of sub-memories, instruction data representing the set of instructions may be stored at a single sub-memory. In other embodiments where the memory 704 comprises a plurality of sub-memories, instruction data representing the set of instructions may be stored at multiple sub-memories. Thus, according to some embodiments, the instruction data representing different instructions may be stored at one or more different locations in the system 700. In some embodiments, the memory 704 may be used to store information, such as the ultrasound image of the fetus, the simulated image of the baby and/or any other data used by the processor 702 of the system 700 or from any other components of the system 700.

The processor 702 can comprise one or more processors, processing units, multi-core processors and/or modules that are configured or programmed to control the system 700 in the manner described herein. In some implementations, for example, the processor 702 may comprise a plurality of (for example, interoperated) processors, processing units, multi-core processors and/or modules configured for distributed processing. It will be appreciated by a person skilled in the art that such processors, processing units, multi-core processors and/or modules may be located in different locations and may perform different steps and/or different parts of a single step of the method described herein.

Briefly, the set of instructions, when executed by the processor 702, cause the processor 702 to acquire an ultrasound image of the fetus. The set of instructions, when executed by the processor 702, further cause the processor 702 to use a machine learning model to generate the simulated image of the baby, based on the ultrasound image of the fetus, wherein the simulated image of the baby comprises a prediction of how the fetus will look as a baby. Acquiring an ultrasound image of a fetus and using a machine learning model to generate a simulated image of a baby were described above with respect to the methods 100 and 500 and the details therein will be understood to apply equally to the operation of the system 700.

It will be appreciated that the system 700 may comprise additional components to those illustrated in FIG. 7. For example, in some embodiments the system 700 may comprise one or more image capture devices, for example for acquiring the ultrasound image of the fetus and/or for acquiring example images of babies for use in training a machine learning model, as described above. Such an image capture device may comprise, for example, a camera or an ultrasound scanner.

The system 700 may further comprise one or more communication interfaces for receiving and/or sending information, for example, to and from a database. The system 700 may further comprise one or more user interfaces such as a display screen, mouse, keyboard or any other user interface allowing information to be displayed to a user or input (such as an ultrasound image or supplementary data relating to a parent of the fetus) to be received from a user. For example, such a display may be used to display the inputs to the machine learning model such as the ultrasound image and/or the supplementary data relating to a parent of the fetus and/or the outputs of the machine learning model, such as the simulated image of the baby, as described above. In some embodiments, the system 700 may further comprise a power source such as a battery or mains power connection.

Figure 8:
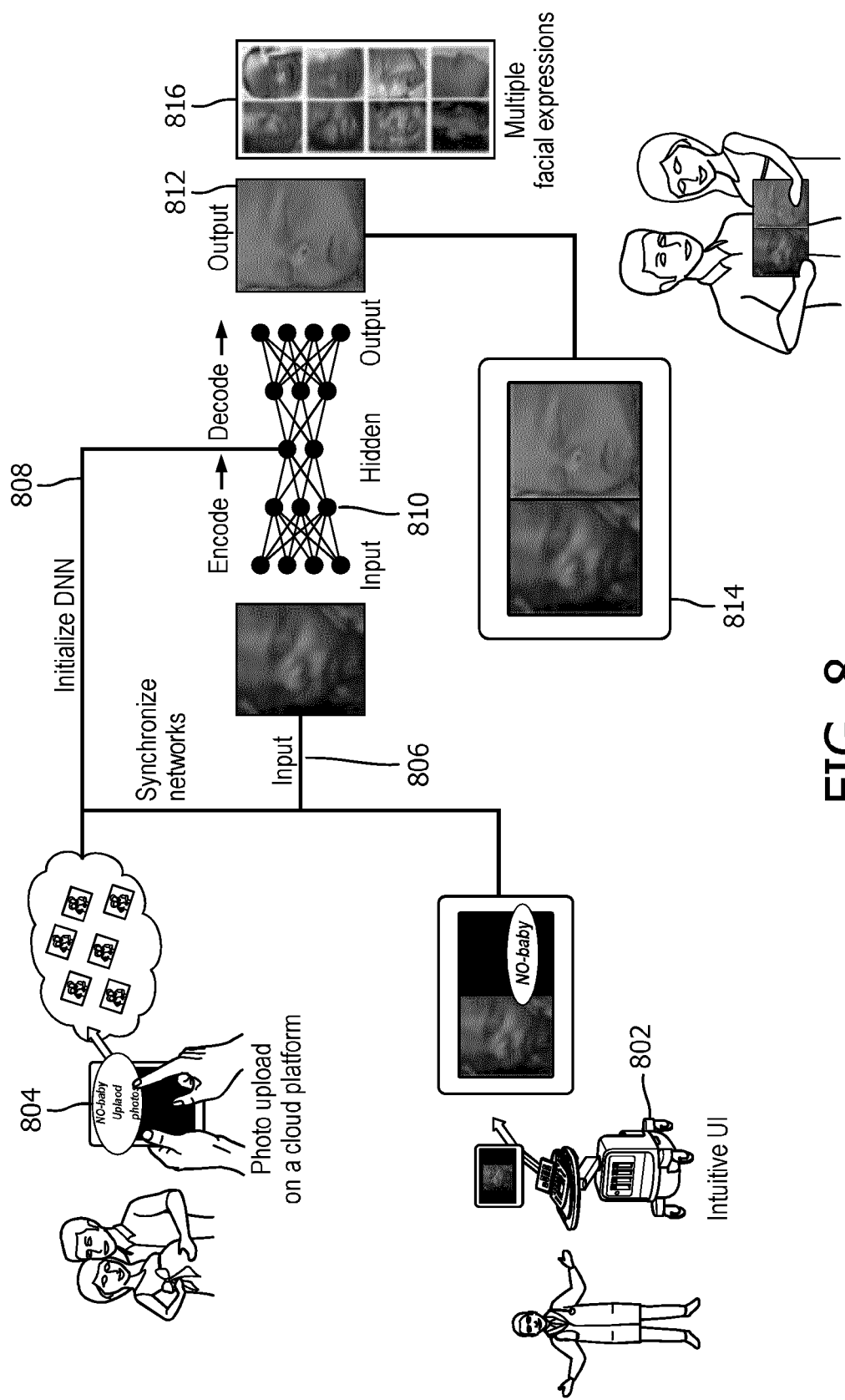
FIG. 8 illustrates an example system for generating a simulated image of a baby based on an ultrasound image of a fetus according to some embodiments.

Turning now to FIG. 8, FIG. 8 illustrates a system for generating a simulated image of a baby based on an ultrasound image of a fetus according to an embodiment. The system of this embodiment comprises an example of one implementation of the system 700 of FIG. 7.

In this embodiment, there is a user interface (UI) 802 for uploading an ultrasound image. The user interface 802 may be embedded directly in an ultrasound scanner or be part of an application that may access ultrasound images obtained from such an ultrasound scanner. There is also an application or "app" 804 (such as a mobile application) for parents or other users. The application 804 may, for example, allow parents or other users to upload supplementary data relating to a parent of the fetus (as described above) and/or one or more photographs of a parent (or other related or non-related person) as a baby.

The user interface 802 may enable a sonographer or other user to synchronize the ultrasound acquisition with the deep learning network (e.g. to trigger the machine learning model to start the prediction process due to the ultrasound data acquisition being complete). In some embodiments, parents or other family members may upload their pictures on a private cloud platform before the scheduled appointment. The synchronization of the 3D ultrasound scan with DNN is necessary to cover all the views/profiles of the fetus, as every input into the network counts to achieve a realistic image (i.e. fetal images showing eyebrows, cheeks, or other facial features). In embodiments where the ultrasound scanner captures vigorous fetal movements, the user interface 802 may further suggest the sonographer switches to 4D imaging to capture the desired images.

The ultrasound image of the fetus is provided as an input 806 to a machine learning model 810 which in this embodiment comprises a variational autoencoder that compresses (encodes) the ultrasound image of the fetus. Any supplementary data provided by the parents of the fetus or other user via the application 804 may be inserted 808 into a hidden layer of the variational autoencoder after which the variational encoder decodes the compressed image to produce an output simulated image of a baby 812. As described above, the simulated image of the baby comprises a prediction of how the fetus may look as a baby.

The resulting simulated image may be displayed alongside the ultrasound image of the baby on a display 814. Multiple facial expressions and/or profile views 816 may be simulated depending on the ultrasound captures.

Turning now to other embodiments, according to some embodiments, there is a computer program product comprising a non-transitory computer readable medium, the computer readable medium having computer readable code embodied therein, the computer readable code being configured such that, on execution by a suitable computer or processor, the computer or processor is caused to perform any of the embodiments of the method 100 or the method 500.

Such a computer program product may be comprised in one or more applications ("apps"). Such a computer program product may be comprised in or installed on one or more devices such as a mobile device, computer, computer tablet or one or more pieces of medical equipment such as an ultrasound scanner. The skilled person will appreciate that these are merely examples and that such a computer program product may be comprised in other devices or applications.

In the manner described above, it may be possible to generate a simulated image of a baby based on an ultrasound image of a fetus, the image of the baby being prediction of how the fetus may look as a baby. Some of the embodiments above are based on the insight that ultrasound images contain information that may be compressed into a lower-dimensionality representation similar to photographs. In some embodiments above, a generative deep learning model converts the image style, perceptual appearance, and texture of the ultrasound image to appear more life-like image, similar to a photograph, whilst enforcing the real content acquired from the ultrasound image. As described above, other supplementary data (e.g. optional information) about the parents may be also used to convert the grayscale ultrasound image into an accurately colored image. These inputs include information about the eye color, hair color, skin tone, race, and others. Because the method does not place requirements on the ultrasound image acquisition strategy, it is also capable of learning the variations in image textures from different devices and even different manufacturers. In this way, predictive images of possible appearances of a fetus after birth may be generated.

The term "module", as used herein is intended to include a hardware component, such as a processor or a component of a processor configured to perform a particular function, or a software component, such as a set of instruction data that has a particular function when executed by a processor.

It will be appreciated that the embodiments herein also apply to computer programs, particularly computer programs on or in a carrier, adapted to put embodiments into practice. The program may be in the form of a source code, an object code, a code intermediate source and an object code such as in a partially compiled form, or in any other form suitable for use in the implementation of the method according to embodiments herein. It will also be appreciated that such a program may have many different architectural designs. For example, a program code implementing the functionality of the method or system according to the embodiments herein may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer implemented method of generating a simulated image of a baby based on an ultrasound image of a fetus, the method comprising:
   acquiring an ultrasound image of the fetus;
   using a machine learning model to generate the simulated image of the baby, based on the ultrasound image of the fetus, wherein the simulated image of the baby comprises a prediction of how the fetus will look as a baby;
   acquiring supplementary data relating to a parent of the fetus; and
   wherein using a machine learning model to generate the simulated image of the baby is further based on the supplementary data.

2. The A method as in claim 1 wherein the simulated image comprises a simulated photographic image.

3. The A method as in claim 2 wherein the simulated photographic image has the appearance of being captured by a digital camera, film camera, or similar medium.

4. The A method as in claim 1 wherein the supplementary data comprises one or more of:
   a characteristic of the parent; and
   a photographic image of the parent as a baby.

5. The A method as in claim 1 wherein the machine learning model generates the simulated image of the baby by combining one or more features of the ultrasound image of the fetus with one or more features derived from the supplementary data.

6. The method as in claim 1 wherein using a machine learning model to generate the simulated image of the baby comprises the machine learning model:
   compressing the ultrasound image to determine the one or more features of the ultrasound image; and
   generating the simulated image of the baby by reconstructing the one or more features of the ultrasound image, using the supplementary data.

7. The method as in claim 6 wherein the machine learning model comprises a variational autoencoder.

8. The method as in claim 1 wherein the supplementary data comprises a photographic image of the parent as a baby; and
   wherein using a machine learning model to generate the simulated image of the baby comprises the machine learning model:
   determining a style related to the photographic image of the parent as a baby;
   determining a content of the ultrasound image; and
   generating the simulated image of the baby by combining the style related to the image of the parent as a baby with the content of the ultrasound image.

9. The method as in claim 8 wherein the machine learning model uses neural artistic style transfer to generate the simulated image of the baby.

10. The method as in claim 1 wherein the simulated image comprises one of:
    a color image; and
    a black and white image.

11. The method as in claim 1 wherein the ultrasound image is generated from three-dimensional or four-dimensional data.

12. A computer implemented method of training a machine learning model to produce a simulated image of a baby based on an ultrasound image of a fetus, the method comprising:
    providing example ultrasound images of fetuses and corresponding example images of the same fetuses as babies;
    training the machine learning model, using the example images, to produce a simulated image of a baby for an ultrasound image of a fetus, wherein the simulated image of the baby comprises a prediction of how the fetus will look as a baby;
    acquiring supplementary data relating to a parent of the fetus; and
    wherein using a machine learning model to generate the simulated image of the baby is further based on the supplementary data.

13. A computer program product comprising a non-transitory computer readable medium, the computer readable medium having computer readable code embodied therein, the computer readable code being configured such that, on execution by a suitable computer or processor, the computer or processor is caused to perform the method of claim 1.

14. A system for generating a simulated image of a baby based on an ultrasound image of a fetus, the system comprising:
    a memory comprising instruction data representing a set of instructions;

a processor configured to communicate with the memory and to execute the set of instructions, wherein the set of instructions, when executed by the processor, cause the processor to:
acquire an ultrasound image of the fetus;
use a machine learning model to generate the simulated image of the baby, based on the ultrasound image of the fetus, wherein the simulated image of the baby comprises a prediction of how the fetus will look as a baby;
acquiring supplementary data relating to a parent of the fetus; and
wherein using a machine learning model to generate the simulated image of the baby is further based on the supplementary data.

* * * * *